(12) United States Patent
Schwartz et al.

(10) Patent No.: US 6,299,893 B1
(45) Date of Patent: Oct. 9, 2001

(54) METHOD TO REDUCE HAIR LOSS AND STIMULATE HAIR REGROWTH

(76) Inventors: Marvin Schwartz, 944 Merritton Road, Pickering Ontario (CA), L1V 1B1; Brian Jeffrey Freund, 1915 Spruce Hill Road, Pickering Ontario (CA), L1V 1S6

(*) Notice: Subject to any disclaimer, the term of this patent is extended or adjusted under 35 U.S.C. 154(b) by 0 days.

(21) Appl. No.: 09/550,604

(22) Filed: Apr. 17, 2000

(51) Int. Cl.[7] .................................................. A61F 13/00

(52) U.S. Cl. .................. 424/422; 424/423; 424/70.1; 514/2; 514/14

(58) Field of Search ................. 514/2, 14, 880; 424/423, 70.1, 422

(56) References Cited

U.S. PATENT DOCUMENTS

| | | | | |
|---|---|---|---|---|
| 4,874,791 | * | 10/1989 | Adachi et al. | 514/558 |
| 5,696,077 | * | 12/1997 | Johnson et al. | 514/2 |
| 5,714,468 | * | 2/1998 | Binder | 514/14 |

* cited by examiner

Primary Examiner—Thurman K. Page
Assistant Examiner—Liliana Di Nola-Baron
(74) Attorney, Agent, or Firm—Dowell & Dowell, P.C.

(57) ABSTRACT

This invention is a method for reduction of hair loss and stimulation of hair growth on the scalp of a human patient. The method comprises the step of administering a presynaptic neurotoxin into the scalp of the patient in a quantity and concentration to provide a therapeutically-effective flaccid paralysis of the muscle tissue outside of the skull of the patient. The result is a reduction in tissue tension in the desired area of hair-growth without affecting any tissue not outside the skull of the patient.

12 Claims, 4 Drawing Sheets

METHOD TO REDUCE HAIR LOSS AND STIMULATE HAIR REGROWTH

BACKGROUND OF INVENTION

The present invention relates to a method of treating the scalp to reduce hair loss and stimulate hair growth on the scalp.

Hair loss on the scalp is a problem that has plagued men and some women since time immemorial. Great effort and expense has been spent trying to prevent and reverse it.

It is now generally appreciated that there are several discernible categories, of hair loss and, logically flowing from the distinctions of the different categories, that each category in and to itself need be separately considered if hair loss reduction or regrowth is desired by any particular person suffering from hair loss.

The most common type of hair loss in men is male pattern baldness or alopecia. Usually with alopecia, hair loss happens gradually over many years. It starts out being most obvious on the crown of the head and in the frontal region in men. For women afflicted with alopecia, the hair loss, which provides a thinning effect, is more spread out and is common after menopause. Despite this type of hair loss being common, it is one of the categories that has met with only very limited success on the part of scalp and hair specialists in being able to reverse its effect.

As a result, in the vast majority of cases, namely males with androgenetic alopecia or, as more commonly referred to as male pattern baldness, short of invasive surgery or hair pieces, effective measures for treatment are very limited.

Nevertheless, in regard to male pattern baldness, there are two medications of which the inventors are aware presently on the market which have shown some success. One of the medications uses as its active ingredient minoxidil and is sold under the product name Rogaine (a trade mark of Pharmacia & Upjohn Company). Rogaine(™) has been shown to reduce hair loss and stimulate hair growth in up to 10 percent of men with male pattern baldness. It is a solution that is applied externally directly to the scalp area and treatment application must be exhaustively and regularly maintained. It is also very expensive.

The other of the medications uses finasteride as an active ingredient and is sold under the product name Propecia (a ™of Merck & Co., Inc.). Propecia(™) is in pill form and taken orally. It also requires consistent application. The pill must be taken on a regular basis.

In both of the above cases, however, the method of action appears uncertain and both require constant attention and application of the user.

There is a need for a method of dealing with alopeccia or male pattern baldness that does not require either of external application, extensive effort or time of the user and which is economical.

It is an object of the present invention to provide a method of dealing with alopeccia or male pattern baldness that does not require external application, that does not require extensive effort of the user and which is economical to use.

SUMMARY OF THE INVENTION

According to an aspect of this invention there is provided a method for reduction of hair loss and stimulation of hair growth on the scalp of a human patient comprising the step of administering a presynaptic neurotoxin into the scalp of the patient in a quantity and concentration to provide a therapeutically-effective flaccid paralysis of the muscle tissue outside of the skull of the patient to reduce tissue tension in the desired area of hair-growth without affecting any tissue not outside the skull of the patient.

BRIEF DESCRIPTION OF THE DRAWINGS

The invention will be more readily understood after reading the following detailed description of the preferred embodiment of the invention in combination with the drawings in which.

DESCRIPTION OF THE PREFERRED EMBODIMENT

Figure 1:
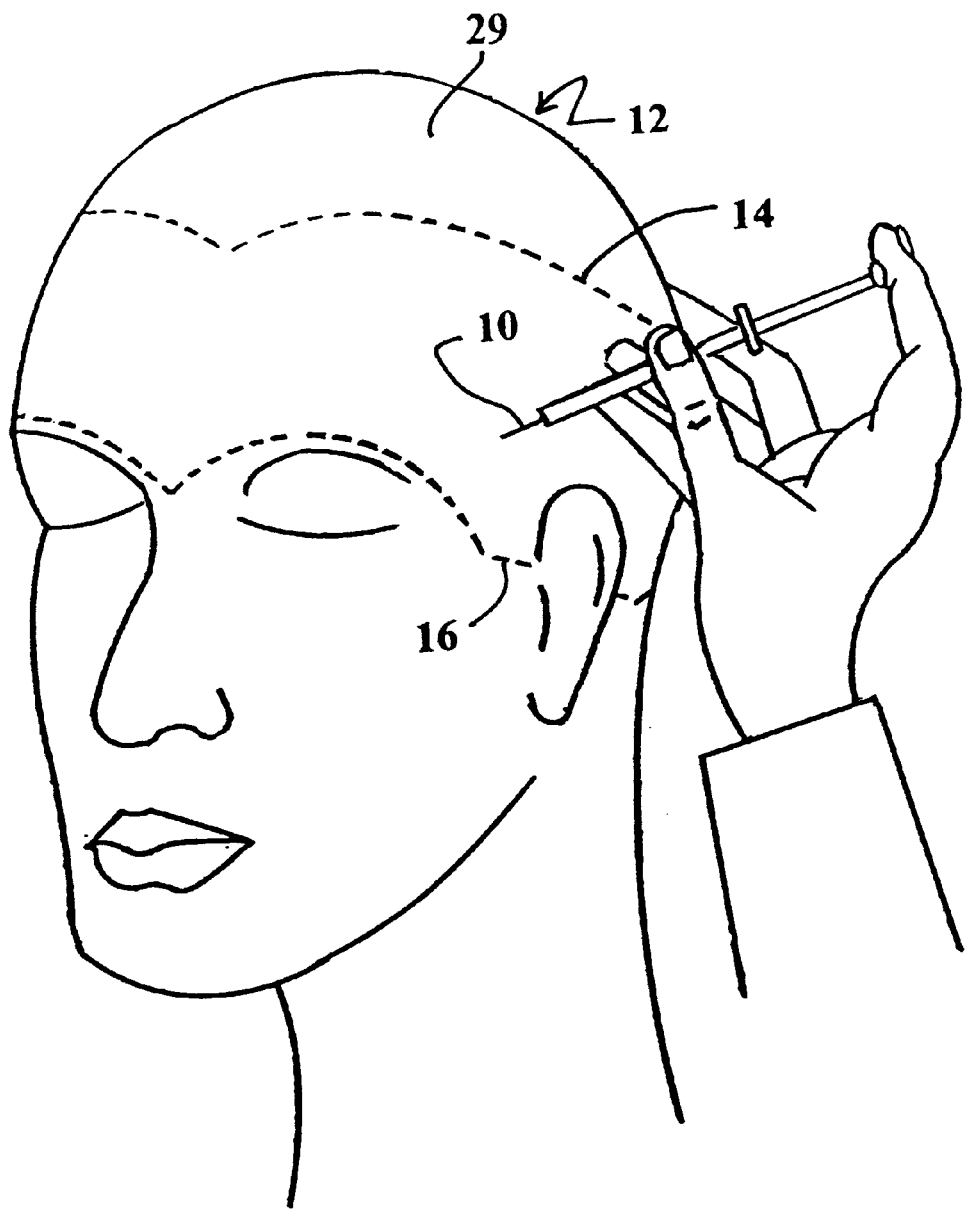
FIG. 1 is illustration of a perspective view of a patient's head showing the administration of an injection into the patient's scalp being made in accordance with the method of this invention.
Figure 2:
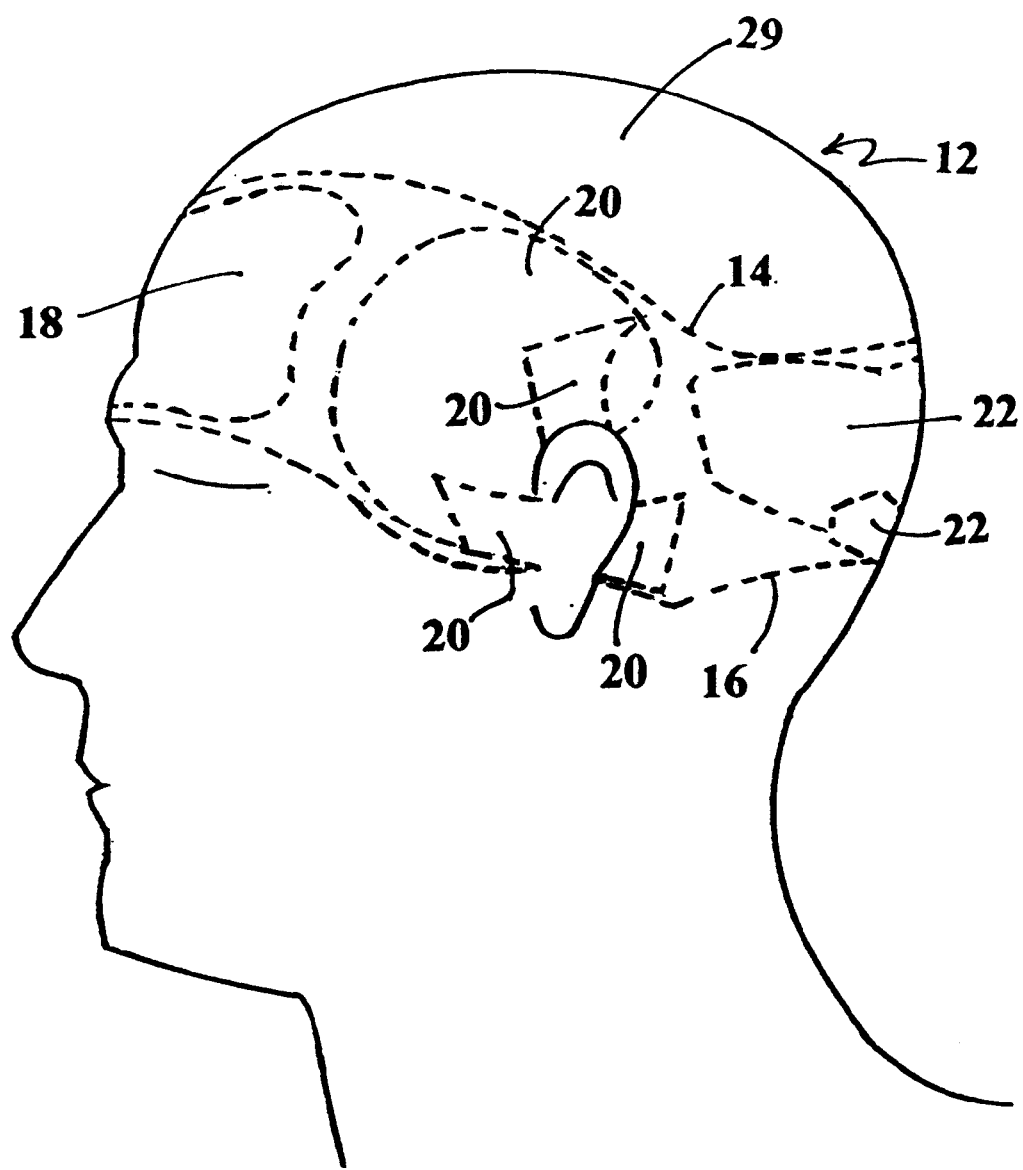
FIG. 2 is an illustration showing the side of the patient's head with the musculature of the side of the scalp outlined in phantom.
Figure 3:
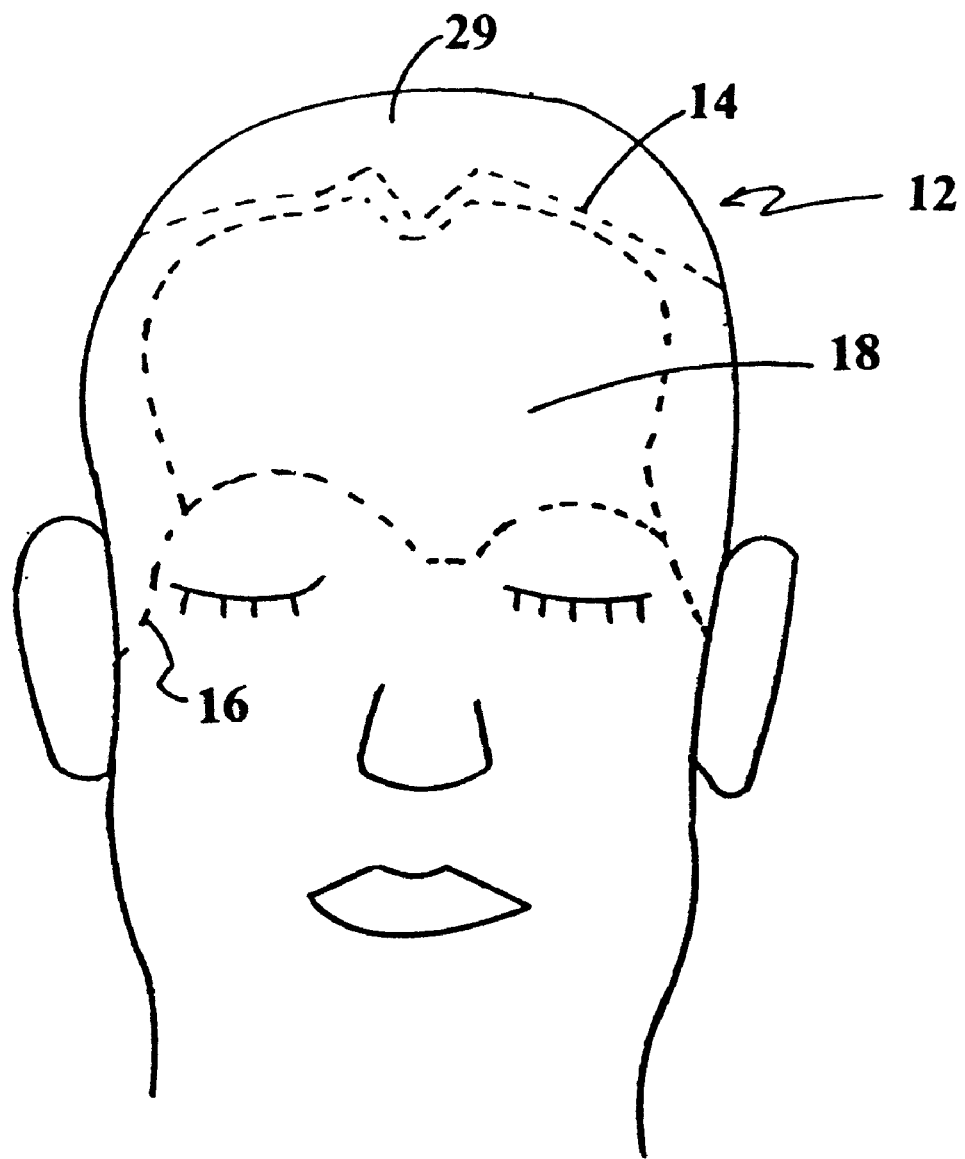
FIG. 3 is an illustration showing the front of a patient's head with the musculature of the front of the scalp outlined in phantom.
Figure 4:
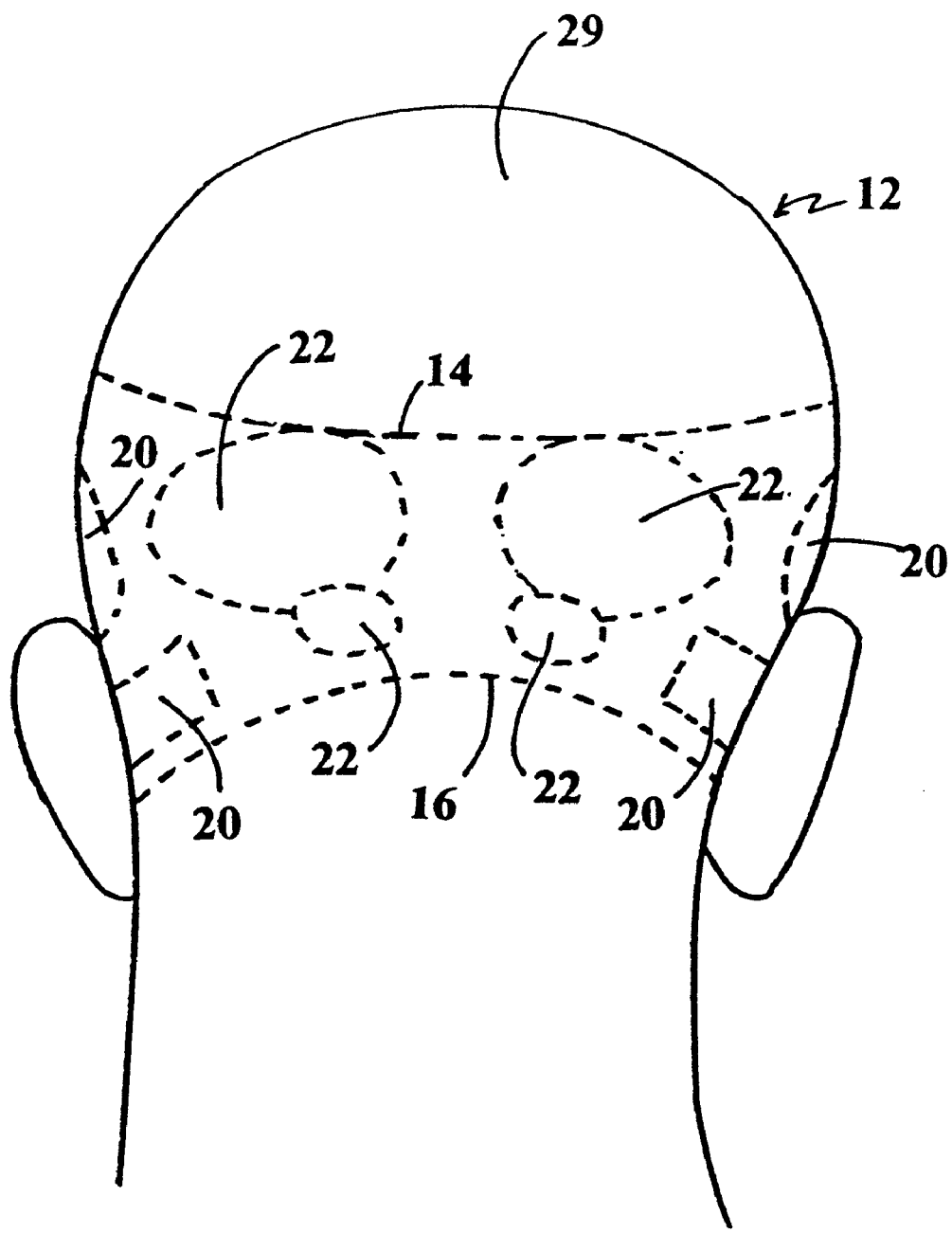
FIG. 4 is an illustration showing the back of a patient's head with the musculature of the back of the scalp outlined in phantom.

Referring to FIG. 1 of the drawings, there is shown the administration of a presynaptic neurotoxin by a qualified health care worker using a hypodermic needle 10 to the scalp of the patient, generally referred to by the numeral 12, in a quantity and concentration, as will be more fully described below, to provide a therapeutically-effective flaccid paralysis of the muscle tissue shown in the area of the band delineated and located approximately between broken lines 14 and 16 in FIGS. 1, 2, 3 and 4, outside of the skull of the patient to reduce tissue tension in the desired area of hair-growth without affecting any tissue not outside the skull of the patient.

Preferably, the presynaptic neurotoxin used is a botulinum toxin, namely botulinim toxin A. Preferably, it is injected, after being reconstituted with normal saline or other suitable and pharmaceutically acceptable carrier or diluent to achieve the desired concentration and volume of injectant, into the frontal muscle as at 18, into the temporal muscles as at 20, and into the occipital muscles as at 22 in a circumferential manner around the periphery of the scalp. As mentioned above, the periphery of the scalp can be represented approximately by a band between broken lines 14 and 16. The exact location of the band will vary with each individual, depending on the location of each individual's scalp musculature. It will be appreciated by those skilled in the art that the peri-auricular group 20 includes the superior auricular muscle as well as the posterior auricular muscle and the anterior portions of the occipital muscle shown in FIG. 3.

Also, in each case, the injections are placed to the areas of the scalp as required for treating the baldness. For effective placing of the injections, the inventors have realized that the anatomy of the scalp can be conceptualized tension-wise as trampoline-like. Over the scalp area, the layers beneath the skin are an unyielding fibrous layer called an aponeurosis (galea aponeurotica). The muscles surrounding the scalp in the band defined by broken lines 14 and 16 are analogous to the springs which would tension and hold taut the tarp of the trampoline. Blood vessels carrying oxygen and nutrients must traverse this area to provide a suitable environment for hair follicles to flourish. When the muscles surrounding the scalp tighten, the areas of scalp mechanically under the highest tension are the vertex and frontal areas. Thus, the most common areas of male pattern baldness correspond to the areas under highest tension. The inventors have found that by reducing the tension of the musculature surrounding the scalp, tension in tissue of the frontal and vertex areas is also effectively reduced. This reduction of tension in the frontal and vertex areas permits an increase of blood flow into that area of the scalp. So it is the ring of musculature surrounding the scalp controls the tension in the target areas. When it is relaxed, the tissue of the whole scalp relaxes. So it is that the tissue in the central area of the scalp 29 is most effectively reduced in tension by reducing muscular tension of the frontal muscles as at 18, into the temporal muscles as at 20, and into the occipital muscles as at 22 in a circumferential manner around the periphery of the scalp. Therefore, a complete circumferential distribution of the toxin present invention around the periphery of the scalp of the person suffering from hair loss is preferable so that a complete circumferential distribution of the toxin is achieved by relaxing the muscle areas responsible for tensioning the underlying tissue of the bald areas.

The object of the injections is to reduce scalp tension. The relative contribution of these muscles to scalp tension will vary in different individuals and, accordingly, it would not be necessary in some individuals to target all these muscle groups to reduce scalp tension. The relative contribution and therefore importance can be readily determined through clinical assessment. Specific factors to be considered would be apparent to the compotent health care worker and depend upon the specific patient, such factors would include scalp muscle bulk and the muscle's ability to move the scalp when contracted voluntarily or by point stimulation.

Diluted botulimim toxin A, the preferred presynaptic neurotoxin, can be deposited in an extra muscular site close to the target muscle but preferably is deposited within the target muscle bodies. As illustrated, it is injected preferably with a fine gauge hypodermic needle or EMG needle but may also be delivered by other modes, acceptable in the art, such as iontophoresis or pneumatic techniques. The muscle to be or affected by administration of presynaptic neurotoxin can be determined or confirmed through digital palpation or through electromyographic guidance.

Subject to the specific situation of the patient, generally each patient can receive injections of approximately 0.1 ml of botulinum toxin diluted to 10 units per 0.1 ml in a pattern whereby a radius of 1.5 cm drawn from the center of the injection site overlaps a similar radius of the adjacent injection site. Reasonably, a larger volume of higher concentration of botulinum toxin A will allow for more space between the injections sites. The number of injections and their spacing over the band defined by broken lines 14 and 16 were, in the case study, were about 1.5 to 3 cm apart and this was found to be effective. The adequacy of the injection technique can be monitored through an objective increase in scalp mobility through digital pressure or through an increase in transcutaneous partial oxygen pressure measurements. A reading taken in the area with hair loss which equals or approaches that of a standardized hair bearing area such as the temporal scalp can be taken as indicative of an adequate response to the technique and therefore adequate performance of the technique.

The administration of the presynaptic neurotoxin produces a reversible, flaccid paralysis of the muscle tissue very local to the area of injection which should remain for a period of three to nine months, if properly administered. The procedure need only be repeated periodically as necessary to maintain laxity of the scalp muscles necessary to permit hair growth. The process therefore requires relatively little effort of the patient and is without the tedious requirement of repetitive application as is the case with some of the proposals in the prior art.

The patient thereby is able to continue on with his life without worry about treatment and need not attend to his scalp except in the normal manner.

It will be appreciated by those skilled in the art that chemicals used as toxins in humans for health purposes must be empirically tested before they can be readily used by the public or by health care workers. The properties of any given chemical in a particular situation cannot be predicted with absolute certainty without proper testing. Although the qualities of the toxin required to achieve the results of the present invention are known and described herein, there is only at this time one toxin known to work and that has been tested. As described in the preferred embodiment, that toxin is botulinim toxin A manufactured by Allegan Inc. of Irvine, Calif. However, other toxins which would imitate botulinim toxin A's qualities in paralyzing muscle tissue safely could also be used. It is the qualities of botulinim toxin A that are desired for this invention and if a substitute toxin with the necessary qualities, as claimed in the broadest claim herein, was to become available, it would be apparent to a person skilled in the art as falling within the scope of this invention.

The tissue environment surrounding the hair follicles is chiefly governed by factors such as local oxygen supply, nutrients and biochemical mediators. The relative concentration of these factors as well as the biochemical reactions they are involved in is quite dependent on the blood supply to the tissues. By using the arterial vessels as described above, blood supply is provided to the central areas of the scalp from the periphery. The inventors have found that injection of a presynaptic neurotoxin improves the tissue environment surrounding the hair follicles by reducing scalp tension and, by doing so, improves bloodflow through the arteries. In turn, the tension in hair-bearing tissue is reduce and hair growth is stimulated.

For illustrative purposes in using the invention, the following is an actual case study in the use of the invention: A healthy 39 year old non-smoker with Hamilton class V male pattern baldness was injected instramuscularly with 100 units BTX-A diluted to 10 units per 0.1 ml in normal saline. The frontal, temporal, peri-auricular and occipital muscles were injected with a fine gauge hypodermic needle in a circumferential manner around the periphery of the scalp as described above. The vertex was photographed as well, position of frontal sentinel hairs and average daily hair loss collected in a fine toothed comb. At 6 months scalp tension increased and a further 100 unite of botulinim toxin A was injected in a manner similar to the first injection. At 1 year, post treatment, daily hair loss was reduced by 76 percent and the frontal sentinel hair was 1 cm forward of its predecessor.

The above example is given to show actual results achieved using this invention and is given for illustrative purposes of its effect.

It will be apparent to those skilled in the art reading this specification as a whole that there are alternatives to following the exact procedure as outlined in the method described as the preferred embodiment herein without deviating from the scope of the invention. It is not intended that the present specification be read in a limiting manner but that the scope of the invention be appreciated as set out in the appended claims.

What is claimed is:

1. A method for reduction of hair loss and stimulation of hair growth on the scalp of a human patient comprising the step of administering a presynaptic neurotoxin into the scalp of the patient in the area of the muscular band extending around the scalp defined by the frontal muscles, temporal muscles, peri-auricular muscles and occipital muscles in a quantity and concentration to provide a therapeutically effective flaccid paralysis of the muscle tissue outside of the skull of the patient to reduce tissue tension inside the area of the muscular band to thereby reduce tissue tension in the desired area of hair-growth on the scalp the perimeter of which is defined by the muscular band without affecting any tissue not outside the skull of the patient.

2. A method for reduction of hair loss and stimulate of hair growth on the scalp of a human patient as claimed in claim 1 wherein the presynaptic neurotoxin is a botulinum toxin.

3. A method for reduction of hair loss and stimulate of hair growth on the scalp of a human patient as claimed in claim 1 wherein the presynaptic neurotoxin is botulinum toxin A.

4. A method for reduction of hair loss and stimulate of hair growth on the scalp of a human patient as claimed in claim 1 wherein the presynaptic neurotoxin is administered by injection with a hypodermic needle.

5. A method for reduction of hair loss and stimulate of hair growth on the scalp of a human patient as claimed in claim 2 wherein the presynaptic neurotoxin is administered by injection with a hypodermic needle.

6. A method for reduction of hair loss and stimulate hair growth on the scalp of a human patient as claimed in claim 3 wherein the presynaptic neurotoxin is administered by injection with a hypodermic needle.

7. A method for reduction of hair loss and stimulate of hair growth on the scalp of a human patient as claimed in claim 1 wherein the presynaptic neurotoxin is administered by injection with a hypodermic needle in a circumferential manner around the periphery of the scalp.

8. A method for reduction of hair loss and stimulate of hair growth on the scalp of a human patient as claimed in claim 2 wherein the presynaptic neurotoxin is administered by injection with a hypodermic needle in a circumferential manner around the periphery of the scalp.

9. A method for reduction of hair loss and stimulate of hair growth on the scalp of a human patient as claimed in claim 3 wherein the presynaptic neurotoxin is administered by injection with a hypodermic needle in a circumferential manner around the periphery of the scalp.

10. A method for reduction of hair loss and stimulate of hair growth on the scalp of a human patient as claimed in claim 1 wherein the presynaptic neurotoxin is administered to the frontal, temporal per-auricular and occipital muscles of the patient.

11. A method for reduction of hair loss and stimulate of hair growth on the scalp of a human patient as claimed in claim 2 wherein the presynaptic neurotoxin is administered to the frontal, temporal peri-auricular and occipital muscles of the patient.

12. A method for reduction of hair loss and stimulate of hair growth on the scalp of a human patient as claimed in claim 3 wherein the presynaptic neurotoxin is administered to the frontal, temporal peri-auricular and occipital muscles of the patient.

* * * * *